United States Patent
Oura et al.

(10) Patent No.: US 9,470,572 B2
(45) Date of Patent: Oct. 18, 2016

(54) METHOD AND APPARATUS FOR MEASURING LIQUID LEVEL OF CELL CULTURE SOLUTION

(71) Applicants: NIHON KOHDEN CORPORATION, Tokyo (JP); TOKYO WOMEN'S MEDICAL UNIVERSITY, Tokyo (JP)

(72) Inventors: Mitsuhiro Oura, Tokyo (JP); Hirotsugu Kubo, Tokyo (JP); Teruo Okano, Tokyo (JP); Tatsuya Shimizu, Tokyo (JP)

(73) Assignees: NIHON KOHDEN CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 487 days.

(21) Appl. No.: 13/848,278

(22) Filed: Mar. 21, 2013

(65) Prior Publication Data

US 2013/0255374 A1 Oct. 3, 2013

(30) Foreign Application Priority Data

Mar. 29, 2012 (JP) ................................. 2012-077791

(51) Int. Cl.
*G01F 23/00* (2006.01)
*G01F 23/292* (2006.01)

(52) U.S. Cl.
CPC .................. *G01F 23/292* (2013.01)

(58) Field of Classification Search
CPC .............................. G01F 23/00; G01F 23/292
USPC ..................................... 73/293; 436/8, 163
See application file for complete search history.

(56) References Cited

U.S. PATENT DOCUMENTS

| | | | |
|---|---|---|---|
| 7,842,509 B2* | 11/2010 | Matsuo et al. | 436/164 |
| 2003/0064005 A1* | 4/2003 | Sasaki et al. | 422/82.05 |
| 2003/0107738 A1* | 6/2003 | Curtis | 356/436 |
| 2007/0141709 A1* | 6/2007 | Albert et al. | 436/8 |
| 2012/0214250 A1* | 8/2012 | Oura et al. | 436/163 |

FOREIGN PATENT DOCUMENTS

| | | |
|---|---|---|
| JP | 61-52274 A | 3/1986 |
| JP | 6-34754 B2 | 5/1994 |
| JP | 2002-257618 A | 9/2002 |
| JP | 2003-294514 A | 10/2003 |
| JP | 5481548 B2 | 4/2014 |

OTHER PUBLICATIONS

Japanese Office Action for the related Japanese Patent Application No. 2012-077791 dated Sep. 29, 2015.

* cited by examiner

*Primary Examiner* — Hezron E Williams
*Assistant Examiner* — Truong Phan
(74) *Attorney, Agent, or Firm* — Kenealy Vaidya LLP

(57) ABSTRACT

A method of measuring a liquid level of a cell culture solution stored in a cell vessel, includes: irradiating the cell culture solution with at least two kinds of light beams including a first light beam having a first wavelength and a second light beam having a second wavelength; measuring a first absorbance of the cell culture solution with respect to the first light beam, and a second absorbance of the cell culture solution with respect to the second light beam; and determining a liquid level of the cell culture solution based on the first absorbance and the second absorbance.

6 Claims, 2 Drawing Sheets

METHOD AND APPARATUS FOR MEASURING LIQUID LEVEL OF CELL CULTURE SOLUTION

CROSS-REFERENCE TO RELATED APPLICATION(S)

This application is based upon and claims the benefit of priority from prior Japanese patent application No. 2012-077791, filed on Mar. 29, 2012, the entire contents of which are incorporated herein by reference.

BACKGROUND

The presently disclosed subject matter relates to a method and apparatus for measuring the liquid level of a cell culture solution stored in a cell vessel.

As a method of determining whether a predetermined amount of a cell culture solution is dispensed to a cell vessel, there is a method in which a change in weight of a cell vessel is measured by using an electric balance. Also, there is another method in which an optical sensor that includes a light emitter and a light receiver is disposed and which uses a phenomenon that, when the liquid level reaches a predetermined level, the intensity of received light is changed (see, for example, JP-A-2003-294514).

An electric balance requires a bulky casing and is expensive. Its measurement value is changed even by a small air flow produced in a measurement space. In the case of the method in which an optical sensor is used, in order to detect plural kinds of liquid levels, it is necessary to dispose optical sensors the number of which is equal to that of the liquid levels. Therefore, the size and cost of a measuring apparatus are unavoidably increased, and the detectable liquid level is inevitably discrete.

SUMMARY

The presently disclosed subject matter may provide a technique in which the liquid level of a cell culture solution can be continuously measured while avoiding increases of the size and cost of a measuring apparatus.

There is provided a method of measuring a liquid level of a cell culture solution stored in a cell vessel, the method comprising: irradiating the cell culture solution with at least two kinds of light beams including a first light beam having a first wavelength and a second light beam having a second wavelength; measuring a first absorbance of the cell culture solution with respect to the first light beam, and a second absorbance of the cell culture solution with respect to the second light beam; and determining a liquid level of the cell culture solution based on the first absorbance and the second absorbance.

The at least two kinds of light beams may be selected from four kinds of light beams having different wavelengths, in accordance with a kind of the cell culture solution.

The cell culture solution may contain: a first material having a first absorption peak within a wavelength region of 300 to 800 nm; and a second material having a second absorption peak or a first convergence point where an absorbance converges to a constant value irrespective of a pH, and a third absorption peak or a second convergence point where an absorbance converges to a constant value irrespective of a pH, within the wavelength region. The four kinds of light beams may include: a light beam having a wavelength corresponding to the first absorption peak; a light beam having a wavelength corresponding to the second absorption peak or the first convergence point; a light beam having a wavelength corresponding to the third absorption peak or the second convergence point; and a light beam having a wavelength at which an absorbance of at least one of the first material and the second material converges to a constant value irrespective of a pH. A pH of the cell culture solution may be determined by measuring absorbances of the cell culture solution with respect to the four kinds of light beams.

The first material may be fetal bovine serum or bovine calf serum, and the second material may be phenol red.

There is provided an apparatus for measuring a liquid level of a cell culture solution stored in a cell vessel, the apparatus comprising: a light emitter which is configured to emit at least two kinds of light beams including a first light beam having a first wavelength and a second light beam having a second wavelength; a light receiver which is configured to receive the least two kinds of light beams that have been passed through the cell culture solution; a measurer which is configured to measure a first absorbance of the cell culture solution with respect to the first light beam, and a second absorbance of the cell culture solution with respect to the second light beam, based on intensities of the at least two kinds of light beams which are received by the light receiver; and a calculator which is configured to determine a liquid level of the cell culture solution based on the first absorbance and the second absorbance.

The light emitter may be placed on a first side of the cell culture solution, and the light receiver may be placed on a second side of the cell culture solution, which is opposite to the first side.

The apparatus may further comprise: a reflector which is configured to reflect the light beams which are emitted from the light emitter. The light emitter and the light receiver may be placed on a first side of the cell culture solution, and the reflector may be placed on a second side of the cell culture solution, which is opposite to the first side.

The light emitter may emit four kinds of light beams having different wavelengths, the measurer may measure absorbances of the cell culture solution with respect to the four kinds of light beams, and the calculator may determine a pH of the cell culture solution based on the absorbances of the cell culture solution with respect to the four kinds of light beams.

DETAILED DESCRIPTION OF EXEMPLARY EMBODIMENTS

Figure 1:
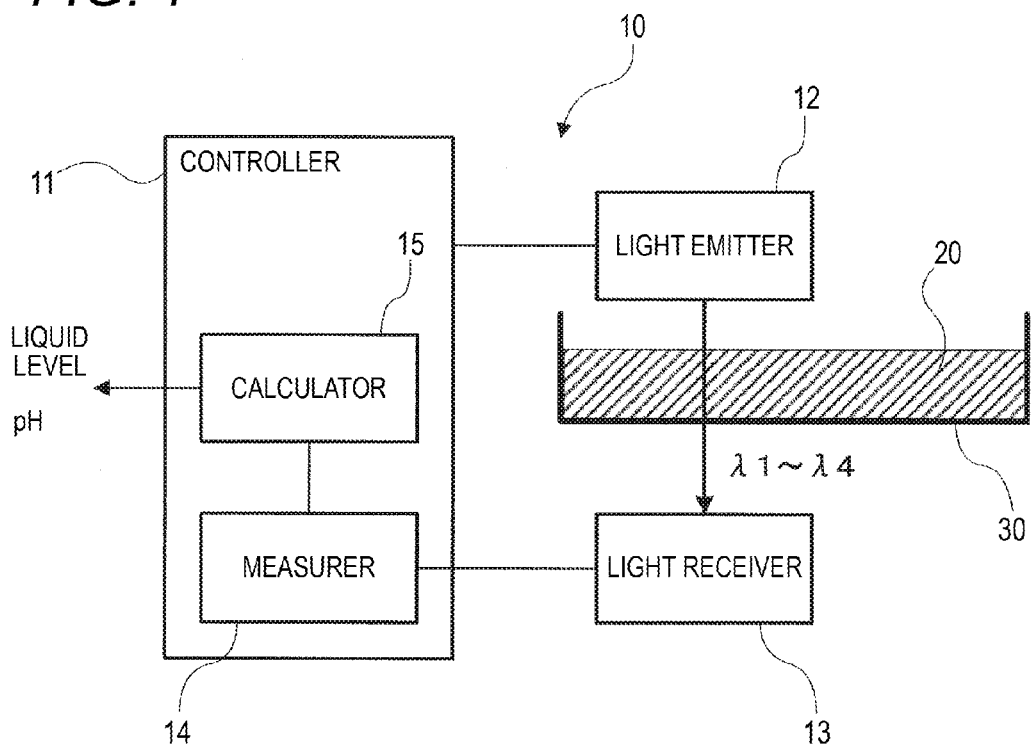
FIG. 1 is a functional block diagram showing the configuration of a measuring apparatus of a first embodiment of the presently disclosed subject matter.

Hereinafter, embodiments of the presently disclosed subject matter will be described in detail with reference to the accompanying drawings. In the drawings which will be referenced in the following description, the scale is adequately changed in order to draw components in a recognizable size.

FIG. 1 is a functional block diagram showing the configuration of a measuring apparatus 10 of a first embodiment of the presently disclosed subject matter. The measuring apparatus 10 includes a controller 11, a light emitter 12, a light receiver 13, a measurer 14, and a calculator 15.

The controller 11 is a calculation processing circuit including a calculation device such as a CPU, and memories such as a RAM and a ROM. The functions of the measurer 14 and the calculator 15 may be realized by an operation of hardware such as circuit devices, that of software such as programs stored in the calculation device, or a combination of these operations.

The light emitter 12 includes a light emitting diode which can emit four kinds of light beams having different wavelengths. The light emitter 12 receives supplies of an electric power and a driving signal from the controller 11, and sequentially emits light beams having respective predetermined wavelengths. The specific values of the wavelengths will be described later.

The light receiver 13 includes a photodiode. The light receiver 13 is configured so as to receive the light beams which are sequentially emitted from the light emitter 12, and output signals which correspond to the intensities of received light beams of the wavelengths, respectively.

In the measuring apparatus 10, a cell vessel 30 storing a cell culture solution 20 is placed between the light emitter 12 and the light receiver 13. Namely, the light emitter 12 is placed on a first side of the cell culture solution 20, and the light receiver 13 is placed on a second side of the cell culture solution 20, which is opposite to the first side. In other words, the light emitter 12 and the light receiver 13 are opposed to each other across the cell culture solution 20.

When the light beams of different wavelengths which are emitted from the light emitter 12 are passed through the cell culture solution 20, the light beams undergo absorption, and their intensities are changed. The measurer 14 measures the absorbance of the cell culture solution 20 with respect to each of the light beams of different wavelengths, based on the intensities of the light beams which are emitted from the light emitter 12, and the intensities of the light beams which are received by the light receiver 13.

The cell culture solution 20 in the embodiment contains fetal bovine serum (FBS) as a first material, and phenol red (PR) as a second material. FBS is a factor for growing cells, and PR is an indicator for detecting the pH of the cell culture solution 20.

The wavelength $\lambda 1$ of the first light beam emitted from the light emitter 12 is determined so that it corresponds to the absorption peak (see FIG. 2) of FBS which is the first absorption peak in the presently disclosed subject matter. Specifically, the wavelength is 411 nm.

The wavelength $\lambda 2$ of the second light beam emitted from the light emitter 12 is determined so that it corresponds to the shorter wavelength absorption peak (see FIG. 2) of PR which is the second absorption peak in the presently disclosed subject matter. Specifically, the wavelength is 430 nm.

The wavelength $\lambda 3$ of the third light beam emitted from the light emitter 12 is determined so that it corresponds to the longer wavelength absorption peak (see FIG. 2) of PR which is the third absorption peak in the presently disclosed subject matter. Specifically, the wavelength is 558 nm.

Figure 2:
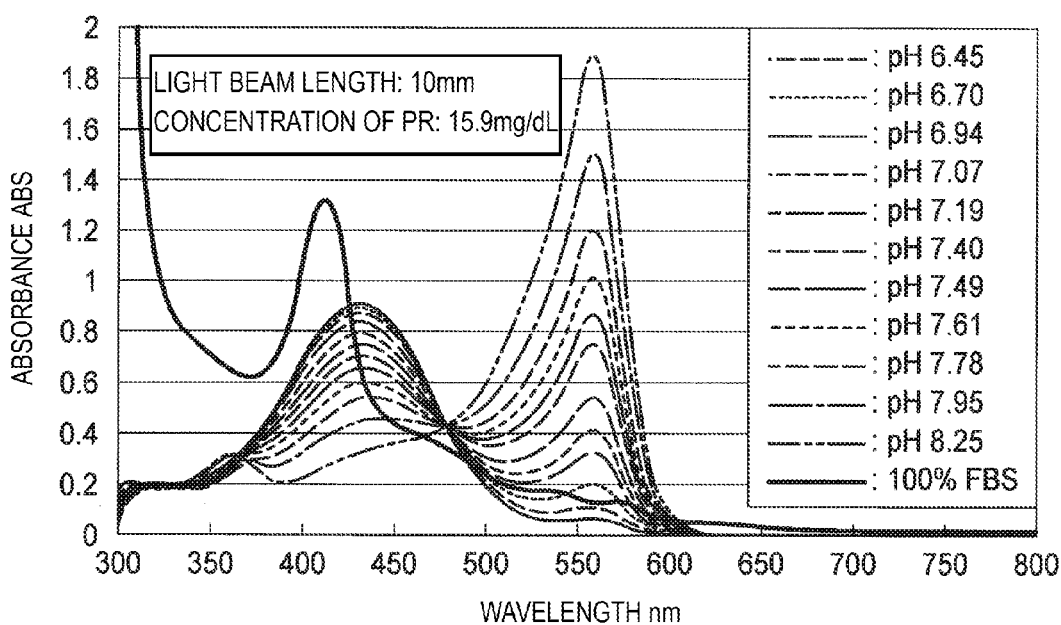
FIG. 2 is a view showing absorption spectra of fetal bovine serum (FBS) and phenol red.

The wavelength $\lambda 4$ of the fourth light beam emitted from the light emitter 12 is determined so that it corresponds to a wavelength at which the absorbances of FBS and PR converge to a constant value irrespective of the pH of the cell culture solution 20 (see FIG. 2). Specifically, the wavelength is 700 nm.

Based on the intensities of the light beams of the wavelengths $\lambda 1$ to $\lambda 4$ which are received respectively by four light receiving elements disposed in the light receiver 13, the measurer 14 measures absorbances $A_{\lambda 1}, A_{\lambda 2}, A_{\lambda 3}, A_{\lambda 4}$ of the cell culture solution 20 with respect to the four kinds of light beams.

Each of the absorbances $A_{\lambda 1}, A_{\lambda 2}, A_{\lambda 3}, A_{\lambda 4}$ of the cell culture solution 20 with respect to the light beams of the different wavelengths is indicated as a sum of the absorbance of FBS, that of PR, and the offset component due to scattering or the like, at the corresponding wavelength as shown in Exp. (1).

$$A_{\lambda 1} = \alpha_{FBS\_\lambda 1} \cdot CF_{FBS} \cdot D\, \alpha_{PR\_\lambda 1} \cdot C_{PR} \cdot D + A_{offset\_\lambda 1}$$

$$A_{\lambda 2} = \alpha_{FBS\_\lambda 2} \cdot C_{FBS} \cdot D + \alpha_{PR\_\lambda 2} \cdot C_{PR} \cdot D + A_{offset\_\lambda 2}$$

$$A_{\lambda 3} = \alpha_{FBS\_\lambda 3} \cdot C_{FBS} \cdot D + \alpha_{PR\_\lambda 3} \cdot C_{PR} \cdot D + A_{offset\_\lambda 3}$$

$$A_{\lambda 4} = \alpha_{FBS\_\lambda 4} \cdot C_{FBS} \cdot D + \alpha_{PR\_\lambda 4} \cdot C_{PR} \cdot D + A_{offset\_\lambda 4} \quad \text{[Exp. (1)]}$$

In the above expressions, $\alpha_{FBS\_\lambda n}$ is the absorption coefficient of FBS with respect to a light beam of the wavelength $\lambda n$, $\alpha_{PR\_\lambda n}$ is the absorption coefficient of PR with respect to the light beam of the wavelength $\lambda n$, $C_{FBS}$ is the concentration of FBS, $C_{PR}$ is the concentration of PR, D is the optical path length (liquid level) related to light absorption, and $A_{offset\_\lambda n}$ is the offset component related to the light beam of the wavelength $\lambda n$.

The relationships between the absorption coefficient $\alpha_{PR\_\lambda 1}$ with respect to the light beam of the wavelength $\lambda 1$ and the absorption coefficients with respect to the other light beams can be approximated by a linear expression. Therefore, Exp. (1) can be deformed as follows.

$$A_{\lambda 1} = \alpha_{FBS\_\lambda 1} \cdot C_{FBS} \cdot D + \alpha_{PR\_\lambda 1} \cdot C_{PR} \cdot D + S_{\lambda 1} \cdot A_{offset}$$

$$A_{\lambda 2} + \alpha_{FBS\_\lambda 2} \cdot C_{FBS} \cdot D + (B_{0\_\lambda 2} \cdot \alpha_{PR\_\lambda 1} + B_{1\_\lambda 2}) \cdot C_{PR} \cdot D + S_{\lambda 2} \cdot A_{offset}$$

$$A_{\lambda 3} = \alpha_{FBS\_\lambda 3} \cdot C_{FBS} \cdot D + (B_{0\_\lambda 3} \cdot \alpha_{PR\_\lambda 1} + B_{1\_\lambda 3}) \cdot C_{PR} \cdot D + S_{\lambda 3} \cdot A_{offset}$$

$$A_{\lambda 4} = \alpha_{FBS\_\lambda 4} \cdot C_{FBS} \cdot D + (B_{0\_\lambda 4} \cdot \alpha_{PR\_\lambda 1} + B_{1\_\lambda 4}) \cdot C_{PR} \cdot D + S_{\lambda 4} \cdot A_{offset} \quad \text{[Exp. (2)]}$$

In the above expressions, $B_{0\_\lambda n}$ is the gradient of a linear expression, $B_{1\_\lambda n}$ is the intercept of the linear expression, and $S\_\lambda n$ is a coefficient with respect to the light beam of the wavelength $\lambda n$.

Exp. (2) can be expressed in the form of a determinant in the following manner.

$$\begin{pmatrix} A_{\lambda 1} \\ A_{\lambda 2} \\ A_{\lambda 3} \\ A_{\lambda 4} \end{pmatrix} = \begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix} \cdot \begin{pmatrix} C_{FBS} \cdot D \\ \alpha_{PR\_\lambda 1} \cdot C_{PR} \cdot D \\ C_{PR} \cdot D \\ A_{offset} \end{pmatrix} \quad \text{[Exp. (3)]}$$

Exp. (3) can be deformed as follows.

$$\begin{pmatrix} C_{FBS} \cdot D \\ \alpha_{PR\_\lambda 1} \cdot C_{PR} \cdot D \\ C_{PR} \cdot D \\ A_{offset} \end{pmatrix} = \begin{pmatrix} \alpha_{FBS\_\lambda 1} & 1 & 0 & S_{\lambda 1} \\ \alpha_{FBS\_\lambda 2} & B_{0\_\lambda 2} & B_{1\_\lambda 2} & S_{\lambda 2} \\ \alpha_{FBS\_\lambda 3} & B_{0\_\lambda 3} & B_{1\_\lambda 3} & S_{\lambda 3} \\ \alpha_{FBS\_\lambda 4} & B_{0\_\lambda 4} & B_{1\_\lambda 4} & S_{\lambda 4} \end{pmatrix}^{-1} \cdot \begin{pmatrix} A_{\lambda 1} \\ A_{\lambda 2} \\ A_{\lambda 3} \\ A_{\lambda 4} \end{pmatrix} \quad \text{[Exp. (4)]}$$

Through the above-mentioned calculations, the calculator 15 determines the liquid level and pH of the cell culture solution 20 based on the absorbances $A_{\lambda 1}$, $A_{\lambda 2}$, $A_{\lambda 3}$, $A_{\lambda 4}$ with respect to the four kinds of light beams. Namely, $C_{PR}$ in $C_{PR} \cdot D$ appearing in the third row of the left-hand side of Exp. (4) is known, and therefore the optical path length (liquid level) D related to light absorption can be determined. D is a value corresponding to the liquid level of the cell culture solution 20.

Figure 3:
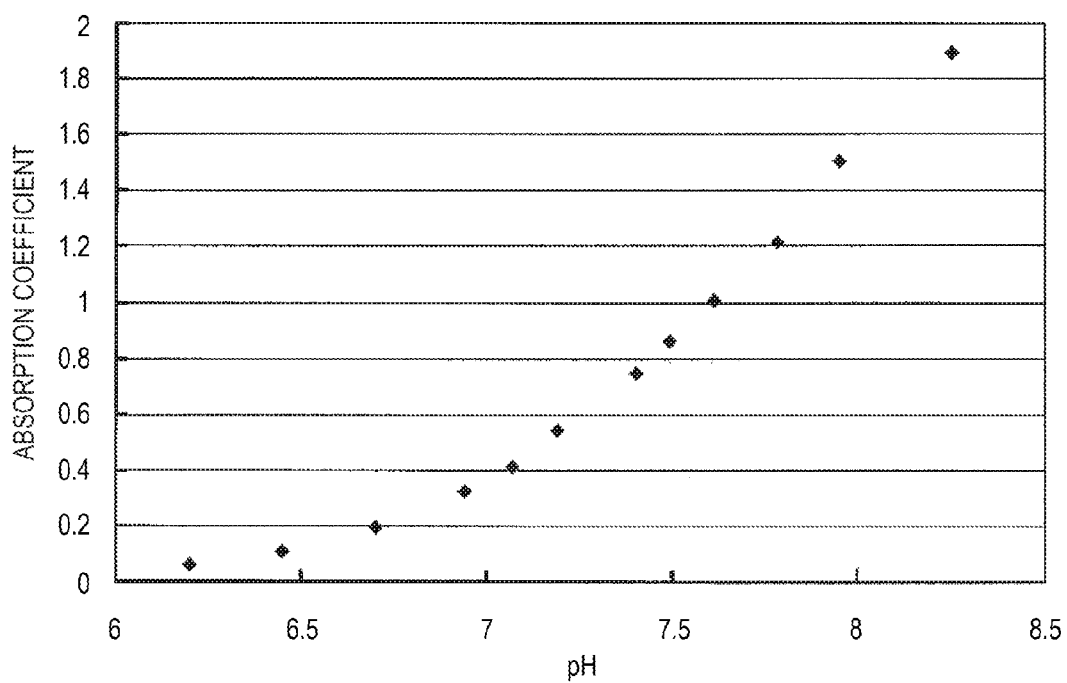
FIG. 3 is a view showing relationships between the absorption coefficient and pH of phenol red with respect to a light beam having a wavelength in the vicinity of 558 nm.

The value of $C_{PR} \cdot D$ in $\alpha_{PR\_\lambda 1} \cdot C_{PR} \cdot D$ appearing in the second row of the left-hand side of Exp. (4) is determined as described above, and therefore the value of the absorption coefficient $\alpha_{PR\_\lambda 1}$ can be determined. The absorption coefficient $\alpha_{PR\_\lambda 1}$ and pH have the relationship shown in FIG. 3, and hence the value of pH of the cell culture solution 20 can be determined.

The determined values of the liquid level and pH are output as data, and then stored in a storage (not shown). Alternatively, the values are displayed on a display (not shown).

According to the embodiment, when the cell culture solution 20 is irradiated with the light beams respectively having the four kinds of wavelengths $\lambda 1$ to $\lambda 4$, and the absorbances $A_{\lambda 1}$ to $A_{\lambda 4}$ with respect to the wavelengths are obtained, therefore, the liquid level of the cell culture solution 20 can be measured. Unlike a related-art level sensor which detects whether the liquid level reaches a predetermined level or not, it is possible to obtain consecutive measurement values. Unlike in an electric balance, the measurement value is not varied by, for example, an air flow produced in a measurement space. Consequently, it is possible to know correctly and rapidly the amount of the cell culture solution 20 which is dispensed to the cell vessel 30.

Consecutive measurement values with respect to the liquid level of the cell culture solution 20 can be obtained simply by disposing one set of the light emitter 12 which can emit the light beams respectively having the four kinds of wavelengths $\lambda 1$ to $\lambda 4$, and the light receiver 13 corresponding thereto. Moreover, the light emitter 12 and the light receiver 13 can be used also in measurement of the pH of the cell culture solution 20. Therefore, the size and cost of the apparatus are not increased.

Figure 4:
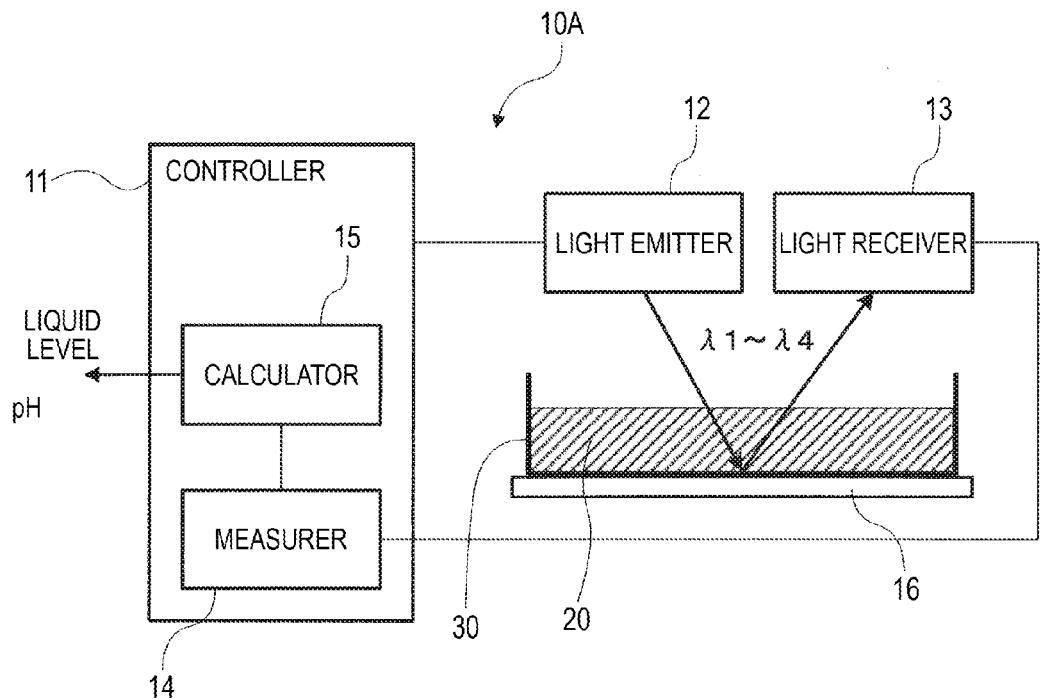
FIG. 4 is a functional block diagram showing the configuration of a measuring apparatus of a second embodiment of the presently disclosed subject matter.

Next, a measuring apparatus 10A of a second embodiment of the presently disclosed subject matter will be described with reference to FIG. 4. The components which are identical or equivalent to those of the measuring apparatus 10 of the first embodiment are denoted by the same reference numerals, and duplicated description is omitted.

In the measuring apparatus 10A, the light emitter 12 and the light receiver 13 are placed above the cell vessel 30. The cell vessel 30 is placed on a mirror 16 which is a reflector that reflects the light beams emitted from the light emitter 12. Namely, the light emitter 12 and the light receiver 13 are placed on the first side of the cell culture solution 20, and the mirror 16 is placed on the second side of the cell culture solution 20, which is opposite to the first side. In other words, the light emitter 12 and the light receiver 13, and the mirror 16 are opposed to each other across the cell culture solution 20.

The light beams of the different wavelengths emitted from the light emitter 12 are passed through the cell culture solution 20 while being reflected by the mirror 16, and then received by the light receiver 13.

According to the configuration, the light emitter 12 and the light receiver 13 can be adjacently placed on the same side in the measurement space. Therefore, driving circuits and the like can be compactly assembled together. This can contribute to further reduction of the size of the apparatus.

The embodiments have been described in order to facilitate understanding of the presently disclosed subject matter, and are not intended to limit the invention. It is a matter of course that the invention may be changed or improved without departing the spirit thereof, and includes equivalents thereof.

In the case where the four kinds of light beams are used, the second and third wavelengths $\lambda 2$, $\lambda 3$ are not limited to those corresponding to the absorption peak of PR. Alternatively, light beams of 367 nm and 479 nm corresponding to a wavelength at which the absorbance of PR converges to a constant value irrespective of the pH may be used.

The number of the wavelengths of the light beams emitted from the light emitter 12 is not limited to four. When unknown parameters in the cell culture solution 20 are reduced, the measuring method of the presently disclosed subject matter can be realized by using at least two kinds of light beams. Therefore, at least two wavelengths of light beams to be used may be selected in accordance with the kind of the cell culture solution 20 which is the measurement object (in accordance with the kind of a known parameter).

When a light beam of 367 nm or 479 nm corresponding to a wavelength at which the absorbance of PR converges to a constant value irrespective of the pH, and that of 700 nm corresponding to a wavelength at which the absorbance of FBS converges to a constant value irrespective of the pH are used, for example, the pH can be eliminated from unknown parameters. Therefore, unknown parameters in Exp. (3) are only D and $A_{offset}$. The following expression is a calculation expression for obtaining them, and the liquid level can be measure by using only two wavelengths or $\lambda 1$ (700 nm) and $\lambda 2$ (367 nm or 479 nm).

$$\begin{pmatrix} D \\ A_{offset} \end{pmatrix} = \begin{pmatrix} \alpha_{FBS\_\lambda 1} \cdot C_{FBS} & S_{\lambda 1} \\ \alpha_{FBS\_\lambda 2} \cdot C_{FBS} + \alpha_{PR\_\lambda 2} \cdot C_{PR} & S_{\lambda 2} \end{pmatrix}^{-1} \cdot \begin{pmatrix} A_{\lambda 1} \\ A_{\lambda 2} \end{pmatrix} \quad \text{[Exp. (5)]}$$

As seen also from the above, the light emitter 12 and the light receiver 13 are not always required to be used also in measurement of the pH.

The first and second materials contained in the cell culture solution 20 are not limited to FBS and PR. The first material may be any material as far as it has an absorption peak within a wavelength region of 300 to 800 nm, and, for example, bovine calf serum may be used as the first material.

The second material may be any material as far as it has two absorption peaks or two points where the absorbance converges to a constant value irrespective of the pH, in the wavelength region of 300 to 800 nm. For example, BPB (bromophenol blue), BTB (bromothymol blue), or the like may be used.

The light emitter 12 which emits plural kinds of light beams is not always required to be configured by a single light emitting element. Alternatively, light emitting elements may be disposed for respective wavelengths. A configuration may be employed where light receiving elements which receive light beams emitted from the light emitting elements are disposed for the light emitting elements, respectively.

According to an aspect of the presently disclosed subject matter, the optical path length (liquid level) related to light absorption can be obtained from plural measured light absorbances. Therefore, consecutive measurement values of the liquid level can be obtained simply by irradiating the cell culture solution with plural kinds of light beams having different wavelengths. Unlike in an electric balance, the measurement value is not varied by, for example, a small air flow produced in a measurement space. Consequently, it is possible to acquire correctly and rapidly the amount of the cell culture solution which is dispensed to the cell vessel. Moreover, a desired measurement value can be obtained simply by disposing one set of the light emitter and the light receiver, and therefore it is possible to avoid increases of the size and cost of the measuring apparatus.

According to an aspect of the presently disclosed subject matter, the pH of the cell culture solution, and the liquid level can be simultaneously measured.

According to an aspect of the presently disclosed subject matter, the light emitter and the light receiver can be used in both measurement of the liquid level of the cell culture solution, and that of the pH. Therefore, this contributes to a reduced size and cost of the apparatus.

What is claimed is:

1. A method of measuring a liquid level of a cell culture solution stored in a cell vessel, the method comprising:
    irradiating the cell culture solution with at least two kinds of light beams including a first light beam having a first wavelength and a second light beam having a second wavelength;
    measuring a first absorbance of the cell culture solution with respect to the first light beam, and a second absorbance of the cell culture solution with respect to the second light beam; and
    determining a liquid level of the cell culture solution based on the first absorbance and the second absorbance,
    wherein the at least two kinds of light beams are selected from four kinds of light beams having different wavelengths, in accordance with a kind of the cell culture solution, and
    wherein the cell culture solution contains:
        a first material having a first absorption peak within a wavelength region of 300 to 800 nm; and
        a second material having a second absorption peak or a first convergence point where an absorbance converges to a constant value irrespective of a pH, and a third absorption peak or a second convergence point where an absorbance converges to a constant value irrespective of a pH, within the wavelength region,
    wherein the four kinds of light beams include:
        a light beam having a wavelength corresponding to the first absorption peak;
        a light beam having a wavelength corresponding to the second absorption peak or the first convergence point;
        a light beam having a wavelength corresponding to the third absorption peak or the second convergence point; and
        a light beam having a wavelength at which an absorbance of at least one of the first material and the second material converges to a constant value irrespective of a pH, and
    wherein a pH of the cell culture solution is determined by measuring absorbances of the cell culture solution with respect to the four kinds of light beams.

2. The method according to claim 1, wherein the first material is fetal bovine serum or bovine calf serum, and the second material is phenol red.

3. An apparatus for measuring a liquid level of a cell culture solution stored in a cell vessel, the apparatus comprising:
    a light emitter which is configured to emit at least two kinds of light beams including a first light beam having a first wavelength and a second light beam having a second wavelength;
    a light receiver which is configured to receive the least two kinds of light beams that have been passed through the cell culture solution;
    a measurer which is configured to measure a first absorbance of the cell culture solution with respect to the first light beam, and a second absorbance of the cell culture solution with respect to the second light beam, based on intensities of the at least two kinds of light beams which are received by the light receiver; and
    a calculator which is configured to determine a liquid level of the cell culture solution based on the first absorbance and the second absorbance,
    wherein the at least two kinds of light beams are selected from four kinds of light beams having different wavelengths, in accordance with a kind of the cell culture solution, and
    wherein the cell culture solution contains:
        a first material having a first absorption peak within a wavelength region of 300 to 800 nm; and
        a second material having a second absorption peak or a first convergence point where an absorbance converges to a constant value irrespective of a pH, and a third absorption peak or a second convergence point where an absorbance converges to a constant value irrespective of a pH, within the wavelength region,
    wherein the four kinds of light beams include:
        a light beam having a wavelength corresponding to the first absorption peak;
        a light beam having a wavelength corresponding to the second absorption peak or the first convergence point;
        a light beam having a wavelength corresponding to the third absorption peak or the second convergence point; and
        a light beam having a wavelength at which an absorbance of at least one of the first material and the second material converges to a constant value irrespective of a pH, and
    wherein a pH of the cell culture solution is determined by measuring absorbances of the cell culture solution with respect to the four kinds of light beams.

4. The apparatus according to claim 3, wherein the light emitter is placed on a first side of the cell culture solution, and the light receiver is placed on a second side of the cell culture solution, which is opposite to the first side.

5. The apparatus according to claim 3, further comprising: a reflector which is configured to reflect the light beams which are emitted from the light emitter, wherein the light emitter and the light receiver are placed on a first side of the cell culture solution, and the reflector is placed on a second side of the cell culture solution, which is opposite to the first side.

6. The apparatus according to claim 3, wherein the light emitter emits four kinds of light beams having different wavelengths, the measurer measures absorbances of the cell culture solution with respect to the four kinds of light beams, and the calculator determines a pH of the cell culture solution based on the absorbances of the cell culture solution with respect to the four kinds of light beams.

* * * * *